United States Patent [19]

Schneider et al.

[11] Patent Number: 5,466,468
[45] Date of Patent: Nov. 14, 1995

[54] PARENTERALLY ADMINISTRABLE LIPOSOME FORMULATION COMPRISING SYNTHETIC LIPIDS

[75] Inventors: Peter Schneider, Bottmingen; Peter van Hoogevest, Riehen; Hans G. Capraro, Rheinfelden, all of Switzerland; Ute Isele, Bad Bellingen, Germany

[73] Assignee: Ciba-Geigy Corporation, Ardsley, N.Y.

[21] Appl. No.: 331,244

[22] Filed: Oct. 28, 1994

Related U.S. Application Data

[60] Continuation of Ser. No. 124,111, Sep. 20, 1993, abandoned, which is a division of Ser. No. 988,399, Dec. 9, 1992, Pat. No. 5,270,053, which is a continuation of Ser. No. 795,406, Nov. 20, 1991, abandoned, which is a continuation-in-part of Ser. No. 674,644, Mar. 25, 1991, abandoned.

[30] Foreign Application Priority Data

Apr. 3, 1990 [CH]  Switzerland ............................. 01104/90

[51] Int. Cl.$^6$ .................................................... A61K 9/127
[52] U.S. Cl. ........................ 424/450; 424/641; 428/402.2; 514/185
[58] Field of Search ..................................... 424/450, 641; 428/402.2; 514/185

[56] References Cited

U.S. PATENT DOCUMENTS 4,774,085  9/1988  Fidler ........................................ 424/855
4,971,802  11/1990  Tarcsay ..................................... 424/450

OTHER PUBLICATIONS

Ginerva et al. Cancer Letters 49, 59, 1990.
Vacha, Acta. Uni. Olomucensis 52, 145, 1969.
Vaduga et al. J. Inorg. Biochem 29, 59 (1987).
Florsheimer et al Thin Solid Films 159, 115 (1988).
Reddy et al. Br. J. Cancer 61, 407 (1990).
Jones et al Thrombosis Res. 39, 711 (1985).

*Primary Examiner*—Gollamudi S. Kishore
*Attorney, Agent, or Firm*—Irving M. Fishman; Karen G. Kaiser

[57] ABSTRACT

The invention relates to pharmaceutical compositions in the form of parenterally, especially intravenously, administrable liposome dispersions or dry preparations, especially lyophilisates, that can be used therefor, comprising the zinc-phthalocyanine complex and synthetic, substantially pure phospholipids.

2 Claims, No Drawings

PARENTERALLY ADMINISTRABLE LIPOSOME FORMULATION COMPRISING SYNTHETIC LIPIDS

This is a continuation of Ser. No. 124,111, filed Sep. 20, 1993, now abandoned, which is a divisional of Ser. No. 988,399, filed Dec. 9, 1992, now U.S. Pat. No. 5,270,053, which is a continuation of Ser. No. 759,406, filed Nov. 20, 1991, now abandoned, which is a continuation in part of Ser. No. 674,644, filed Mar. 25, 1991, now abandoned.

The invention relates to pharmaceutical compositions in the form of parenterally administrable liposome dispersions, or dry preparations that can be used therefor, comprising the zinc-phthalocyanine complex and synthetic, substantially pure phospholipids, to a novel inventive process for the preparation of those pharmaceutical compositions and to the use of the dry preparations for the preparation of intravenously administrable liposome dispersions and to the use of the zinc-phthalocyanine complex and the synthetic, substantially pure phospholipids for the preparation of dry preparations. The invention relates also to the use of the pharmaceutical compositions in a method for the therapeutic treatment of the human or animal body.

Both the zinc-phthalocyanine complex itself and its therapeutic use in photodynamic chemotherapy for the treatment of tumours are known, see J. D. Spikes. Photochem. Photobiol. 43, 691 (1986). The zinc-phthalocyanine complex is administered intraperitoneally to mice or rats in vivo in the form of an aqueous suspension and the carcinoma induced in the experimental animals is irradiated with high-energy light, preferably with concentrated visible light (LASER).

The use of intraperitoneal dosage forms in human therapy generally gives rise to problems because of the pain caused by the piercing of the abdominal cavity and the great demands made of the skill of the physician. Attempts are therefore being made to find an alternative parenteral dosage form which is more acceptable to the patient, but which is also capable of ensuring systemic distribution of the zinc-phthalocyanine complex to be administered.

The intravenous dosage form offers systemic distribution of the active ingredient but requires the active ingredient to be homogeneously distributed in the aqueous injection fluid.

For the preparation of suitable intravenous dosage forms it has therefore been proposed to use instead of the sparingly soluble zinc-phthalocyanine complex the water-soluble derivatives thereof and to administer those derivatives intravenously, see J. Rousseau et al., Int. J. Appl. Radiat. Isot. 36, 709 (1985).

Although the introduction of hydrophilic groups, such as sulfonyl groups, into the porphyrin nucleus of the zinc-phthalocyanine complex increases the water-solubility of the complex, the derivatives obtained are of a poor standard and are unsuitable for pharmaceutical use since they consist of non-uniform mixtures of the mono- to tetra-substituted derivatives with several regioisomers, see F. H. Moser et al., The Phthalocyanines, CRC Press, 1983, Vol. II, page 20. The separation of the numerous isomeric derivatives would involve unrealistic expenditure.

As an alternative it has been proposed to solubilise the chemically pure, water-insoluble zinc-phthalocyanine complex in aqueous phase by the addition of a vehicle. For example, using suitable solubilisers in the form of phospholipids, for example dipalmitoylphosphatidyl choline, the complex can be encapsulated in unilamellar liposomes which are substantially homogeneously dispersible in aqueous phase, see E. Reddi et al., Br. J. Cancer (1987), 56, pages 597–600.

This homogeneous liposome dispersion is nevertheless still unsuitable for the purposes of intravenous administration to humans because the dispersion is prepared in accordance with the so-called injection method using relatively large amounts of toxic pyridine, see G. Valduga et at., J. Inorg. Biochem. 29, 59–65 (1987). Pyridine is one of the few solvents in which the zinc-phthalocyanine complex is at all soluble. That solution is diluted with ethanol and the pyridine-containing ethanolic solution is injected at elevated temperature into water or buffer solution. In accordance with that method a residue of the toxic solvent pyridine will always remain in me aqueous phase as a result of the formation of an azeotropic mixture.

The preparation of liposome dispersions by other methods that do not use organic solvents also gives rise to problems. Even when solvent-free dry preparations, such as lyophilisates or evaporation residues, are used for the formation of the aqueous liposome dispersions, the preparation of those dry preparations can in turn be effected only from solutions in selected organic solvents or solvent mixtures because of the lipophilic nature and the water-insolubility of the lipid components. Both the zinc-phthalocyanine complex and the phospholipids used have to be completely soluble in those solvents. The evaporation of the solvents must result in a homogeneous and pourable powder. The components must not be allowed to separate, as this would result in the agglutination of the dry preparation and the formation not of liposomes but only of poorly dispersible aggregates, for example large micelles, which could cause embolisms.

The problem underlying the present invention is to prepare a parenterally, especially intravenously, administrable liposome dispersion using those solvents in which the zinc-phthalocyanine complex and the phospholipid components are completely soluble and of which the residual amount consisting of unremovable solvent residues is less than 1%, which amount is toxicologically harmless for intravenous formulations.

The invention relates to pharmaceutical compositions in the form of parenterally administrable liposome dispersions comprising a) the zinc-phthalocyanine complex, b) a synthetic, substantially pure phospholipid of formula

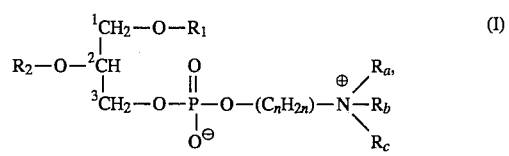

wherein $R_1$ is $C_{10}$–$C_{20}$alkanoyl having an even number of carbon atoms, $R_2$ is $C_{10}$–$C_{20}$alkenoyl having an even number of carbon atoms, $R_a$, $R_b$ and $R_c$ are hydrogen or $C_1$–$C_4$alkyl and n is an integer from two to four, optionally combined with a c) synthetic, substantially pure phospholipid of formula

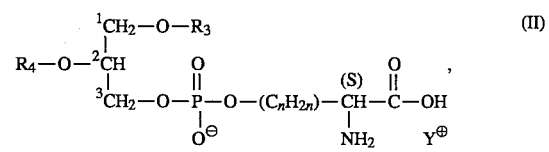

wherein $R_3$ and $R_4$ are each independently of the other $C_{10}$–$C_{20}$alkenoyl having an even number of carbon atoms, n is an integer from one to three and $Y^\oplus$ is the cation of a pharmaceutically acceptable base, and d) a pharmaceutically acceptable carrier liquid and, optionally, water-soluble excipients suitable for parenteral dosage forms.

The terms and definitions used hereinabove and hereinbelow preferably have the following meanings in the context of the description of the invention:

The term "pharmaceutical composition" defines a mixture of substances that is suitable for parenteral administration, in the present case especially for intravenous administration, to humans and animals, preferably to humans, and that can be used for the treatment of various diseases, in the present case tumours.

The parenterally administrable liposome dispersion comprises liposomes in the form of unilamellar, multilamellar, large and small liposomes consisting of a double-layer arrangement of phospholipids (I) and optionally (II) having an interior space and a spherical shape (unilamellar) or consisting of several concentric double-layer arrangements of phospholipids (I) and optionally (II) having an interior space and a spherical shape ("onion-skin" structure of the double layers or membranes-multilamellar). The size of the liposomes varies from approximately $1.0 \times 10^{-8}$ to approximately $1.0 \times 10^{-5}$ m, depending upon the preparation process.

The therapeutic use of liposomes as careers of active ingredients of different kinds is known. For example, liposomes have been proposed as carriers of proteins, for example antibodies or enzymes, hormones, vitamins or genes, or, for analytical purposes, as carriers of labelled compounds.

Pharmaceutical dosage forms based on liposomes are described in the synoptical work by Gregoriadis G. (Ed.) Liposome Technology, Vol. II, Incorporation of Drugs, Proteins and Genetic Material, CRC Press 1984. In the synoptical work by Knight, C. G. (Ed.), Liposomes: From Physical Structure to Therapeutic Applications, Elsevier 1981, the advantages of a pharmaceutical dosage form based on liposomes are summarised in Chapter 16, page 166.

The liposome dispersion according to the present invention is free of solid particles and larger lipid aggregates, is stable to storage even at room temperature for several days to weeks, is reproducible as regards the proportion of the components, is toxicologically harmless as regards the lipid components used and the residual amounts of organic solvents, and on the basis of findings in vitro and in vivo is suitable for parenteral, especially intravenous, administration to humans.

Unless expressly defined otherwise, the term "lower" used in connection with organic radicals, for example lower alkyl, lower alkylene, lower alkoxy, lower alkanoyl etc., indicates that the organic radicals so designated contain up to and including 7, and preferably up to and including 4, carbon atoms.

The nomenclature for the phospholipids of formulae I and II and the numbering of the carbon atoms is in accordance with the recommendations made in the Eur. J. of Biochem. 79, 11–21 (1977) "Nomenclature of Lipids" by the IUPAC-IUB Commission on Biochemical Nomenclature (CBN) (sn-nomenclature, stereospecific numbering).

The zinc-phthalocyanine complex a) corresponds to the compound described on page 1 of the publication by G. Valduga et al., Photochem. and Photobiology Vol. 48, No. 1 (1988), pages 1–5, which compound has been known for a long time.

The purity of the synthetic phospholipids of formulae I and II is more than 90%, but preferably more than 95%, by weight.

This degree of purity can be demonstrated by known analytical methods, for example by chromatography, such as HPLC, gas chromatography or paper chromatography.

In a phospholipid of formula I, $R_1$ as "$C_{10}$–$C_{20}$alkanoyl having an even number of carbon atoms" is preferably n-dodecanoyl, n-tetradecanoyl, n-hexadecanoyl, n-octadecanoyl or n-icosanoyl.

In a phospholipid of formula I, $R_2$ as "$C_{10}$–$C_{20}$alkenoyl having an even number of carbon atoms" is preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl or 9-cis-icosenoyl.

In a phospholipid of formula I, $R_a$, $R_b$ and $R_c$ are preferably $C_1$–$C_4$alkyl, especially methyl.

In a phospholipid of formula I, n is an integer from two to four, preferably two. The group of the formula —$(C_nH_{2n})$— is unbranched or branched alkylene, for example 1,1-ethylene, 1,1-, 1,2- or 1,3-propylene or 1,2-, 1,3- or 1,4-butylene. 1,2-ethylene (n=2) is preferred.

In an especially preferred phospholipid of formula I, $R_1$ is n-dodecanoyl, n-tetradecanoyl, n-hexadecanoyl or n-octadecanoyl and $R_2$ is 9-cis-dodecenoyl, 9-cis-tetradecenoyl, 9-cis-hexadecenoyl, 9-cis-octadecenoyl or 9-cis-icosenoyl, $R_a$, $R_b$ and $R_c$ are methyl and n is two.

A very especially preferred phospholipid of formula I is synthetic 1-n-hexadecanoyl-2-(9-cis-octadecenoyl)-3-sn-phosphatidyl choline having a purity of more than 90%, but preferably more than 95%.

In a phospholipid of formula II, $R_3$ and $R_4$ are as defined for $R_1$ and $R_2$ under formula I.

In a phospholipid of formula II, $R_3$ and $R_4$ as "$C_{10}$–$C_{20}$alkenoyl having an even number of carbon atoms" are preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl or 9-cis-icosenoyl.

The cation $Y^\oplus$ of a pharmaceutically acceptable base is, for example, an alkali metal ion, for example the lithium, sodium or potassium ion, the ammonium ion, a mono-, di- or tri- $C_1$–$C_4$alkylammonium ion, for example the trimethyl-, ethyl-, diethyl- or triethyl-ammonium ion, the tetramethylammonium ion, a 2-hydroxyethyl-tri-$C_1$–$C_4$alkylammonium ion, for example the choline cation, or the 2-hydroxyethylammonium ion, or the cation of a basic amino acid, for example lysine or arginine.

$Y^\oplus$ is preferably the sodium ion.

In an especially preferred phospholipid of formula II, $R_3$ and $R_4$ are identical and are, for example, 9-cis-dodecenoyl, 9-cis-tetradecenoyl, 9-cis-hexadecenoyl, 9-cis-octadecenoyl or 9-cis-icosenoyl, n is one and $Y^\oplus$ is the sodium ion.

A very especially preferred phospholipid of formula II is synthetic sodium 1,2-di(9-cis-octadecenoyl)-3-sn-phosphatidyl S-serine having a purity of more than 90%, but preferably more than 95%.

The names given in parenthesis are also customary for the acyl radicals in the phospholipids of formulae I and II: 9-cis-dodecenoyl(lauroleoyl), 9-cis-tetradecenoyl(myristoleoyl), 9-cis-hexadecenoyl(palmitoleoyl), 6-cis-octadecenoyl(petroseloyl), 6-trans-octadecenoyl(petroselaidoyl), 9-cis-octadecenoyl(oleoyl), 9-trans-octadecenoyl(elaidoyl), 11-cis-octadecenoyl(vaccenoyl), 9-cis-icosenoyl(gadoleoyl), n-dodecanoyl(lauroyl), n-tetradecanoyl(myristoyl), n-hexadecanoyl(palmitoyl), n-octadecanoyl(stearoyl), n-icosanoyl(arachidoyl).

In the pharmaceutically acceptable career liquid d) the components a) and b) or a), b) and c) are present in the form of liposomes, preferably multilamellar liposomes, in such a manner that for several days or weeks there is no re-formation of solids or solid aggregates, such as micelles, and the clear or in some cases slightly opalescent liquid comprising the said components can be administered, if necessary after filtration, parenterally, preferably intravenously.

The carrier liquid d) may comprise, for example, pharmaceutically acceptable, non-toxic water-soluble excipients that are necessary, for the establishment of isotonic conditions, for example ionic additives, such as sodium chloride or non-ionic additives (structure formers), such as sorbitol, mannitol, glucose or lactose. In particular, the dry, preparation comprises those additives, for example sodium chloride or mannitol, in the prescribed amounts, which are necessary, for the establishment of isotonic conditions in the parenterally administrable solutions.

Suitable water-soluble excipients in the solution and in the dry, preparation are also wetting agents or surfactants in the true sense that can be used for liquid pharmaceutical formulations, especially non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters such as polyoxyethylene sorbitan monolaurate, monooleate, monostearate, monopalmitate, tristearate or trioleate, polyethylene glycol fatty acid esters, such as polyoxyethyl stearate. polyethylene glycol 410 stearate, polyethylene glycol 2000 stearate, especially ethylene oxide/propylene oxide block polymers of the Pluronic® type (Wyandotte Chem. Corp.) or Synperonic® type (ICI).

The liposome dispersion can be prepared from a dry, preparation to which the present invention likewise relates.

The present invention relates also to pharmaceutical compositions in the form of a dry preparation comprising a) the zinc-phthalocyanine complex, b) a synthetic, substantially pure phospholipid of formula I wherein $R_1$, $R_2$, $R_a$, $R_b$ and $R_c$ and also n are as defined above, optionally combined with a c) synthetic, substantially pure phospholipid of formula II wherein $R_3$, $R_4$, n and $Y^\oplus$ are as defined above, and optionally d) water-soluble excipients suitable for intravenous dosage forms.

A dry preparation is the residue obtainable after any thermal drying process, such as evaporation at room temperature or elevated temperature or, preferably, freeze-drying, which residue contains less than 1% (by weight), preferably less than 0.5%, organic solvent residues, such as piperidine, tert-butanol or dimethyl sulfoxide.

In the dry preparation, the zinc-phthalocyanine complex is present in a ratio of approximately from 0.1 to 5.0% by weight, preferably from 0.1 to 1.0% by weight, based on the total amount of phospholipids of formulae I and optionally II—components b) and optionally c). In the dry preparation the mixing ratio of the phospholipids of formula I—the lecithin component—to the phospholipids of formula II—the serine component—is approximately from 60:40% to 95:5% by weight, preferably from 70:30% to 90:10% by weight, and most preferably from 80:20% to 90:10% by weight.

The dry preparation of the present invention is distinguished by good filling properties, exact reproducibility of the weighed amounts introduced into the unit dose forms and storage stability.

The present invention relates also to a process for the preparation of a pharmaceutical composition in the form of a parenterally administrable liposome dispersion, which process comprises dispersing in aqueous phase a dry preparation comprising a) the zinc-phthalocyanine complex, b) a synthetic, substantially pure phospholipid of formula I, wherein $R_1$, $R_2$, $R_a$, $R_b$ and $R_c$ and also n are as defined above, optionally combined with a c) synthetic, substantially pure phospholipid of formula II, wherein $R_3$, $R_4$, n and $Y^\oplus$ are as defined above, and optionally d) water-soluble excipients suitable for parenteral dosage forms and optionally buffering the resulting aqueous dispersion to pH 7.0–7.8 and/or isolating a liposome fraction having a desired diameter range.

The individual steps of the process are carried out in a manner known per se by reconstituting the dry preparation obtainable in accordance with the invention, prior to administration in the form of a liposome dispersion, in the prescribed amount of liquid, especially in sterile (pyrogen-free) water for injection.

Dispersion is effected, for example, by shaking (for example using a Vortex mixer) or stirring the aqueous phase to which the dry preparation has previously been added. The formation of liposomes, which may be large, small, unilamellar or multilamellar, takes place spontaneously, that is to say without the additional supply of external energy and at great speed. It is possible to disperse approximately from 0.1 to 50% by weight (based on the total weight of the aqueous dispersion), preferably from 2 to 20% by weight, of the dry preparation in aqueous phase.

Aqueous dispersions having an acidic or basic reaction are preferably buffered to pH 7.0–7.8, preferably pH 7.2–7.4. Optionally dispersion is effected in an aqueous buffer solution that has already been buffered to that pH value.

Dispersion is effected at temperatures of below approximately 36° C., preferably at room temperature. As appropriate, the process is carried out with cooling and/or under an inert gas atmosphere, for example a nitrogen or argon atmosphere. The resulting liposomes are stable in aqueous phase over a very long period (up to several weeks or months).

The size of the liposomes formed depends inter alia upon the amount of active ingredient and the lipid components, the mixing ratio thereof and the concentration of the components in the aqueous dispersion and upon the method of preparation. For example, by increasing or reducing the concentration of lipid components it is possible to produce aqueous phases having a high proportion of small or large liposomes.

It is possible to obtain an especially uniform size distribution of the liposomes by aftertreatment of the liposome dispersion, for example by treatment with ultrasound or extrusion through straight-pored filters (for example Nucleopore®).

The separation and isolation of a fraction of large liposomes from a traction containing small liposomes, insofar as it is at all necessary, is effected by means of conventional separation methods, for example gel filtration, for example with Sepharose® 4B or Sephacryl® (Pharmacia SE) as carrier, or by sedimentation of the liposomes in an ultracentrifuge, for example with a gravitational field of 160,000×g. For example, after centrifugation for several hours, for example about three hours, in that gravitational field, large liposomes are deposited, whereas small liposomes remain in dispersion and can be decanted. Repeated centrifugation results in complete separation of the large liposomes from the small liposomes.

Gel filtration especially can be used to separate off all the liposomes present in the aqueous phase having a diameter of more than about $6.0 \times 10^{-8}$ m and also non-encapsulated components and excess, dispersed lipids that are present in high molecular weight aggregates and thus to produce an aqueous dispersion having a fraction of liposomes of relatively uniform size.

The completed formation of liposomes and their content in aqueous phase can be demonstrated in a manner known per se by various physical measuring methods, for example with freeze fracture samples and thin sections under an electron microscope or by X-ray diffraction, by dynamic light scattering, by mass determination of the filtrate in an analytical ultracentrifuge and especially by spectroscopy, for example in the nuclear resonance spectrum ($^1$H, $^{13}$C and $^{31}$P).

The present invention relates also to a novel, inventive process for the preparation of a pharmaceutical composition in the form of a dry preparation, which process comprises dissolving a) the zinc-phthalocyanine complex and b) a synthetic, substantially pure phospholipid of formula I, wherein $R_1$, $R_2$, $R_a$, $R_b$ and $R_c$ and also n are as defined above, optionally combined with a c) synthetic, substantially pure phospholipid of formula II, wherein $R_3$, $R_4$, n and $Y^\oplus$ are as defined above, in a pharmaceutically acceptable organic solvent, the residual amount of which in a dry preparation is toxicologically harmless, and optionally d) adding carrier liquid and water-soluble excipients suitable for parenteral dosage forms, and removing the solvent or solvent mixture.

A pharmaceutically acceptable organic solvent, the residual amount of which in a dry preparation is toxicologically harmless, is suitable for the preparation of a clear solution of the zinc-phthalocyanine complex and if possible the phospholipid components (I) and (II). If the phospholipids are insoluble in the organic solvent in which the zinc-phthalocyanine complex is soluble, they are dissolved in a second solvent, for example in tert-butanol, and that solution is combined with the solution of the zinc-phthalocyanine complex.

Preferred organic solvents that meet the toxicological requirements as regards the residual amounts present in the dry preparation and in which the zinc-phthalocyanine complex is soluble are dimethyl sulfoxide, N-methyl-2-pyrrolidone and piperidine, and mixtures thereof.

The zinc-phthalocyanine complex is soluble in dimethyl sulfoxide and N-methyl-2-pyrrolidone (NMP) but the phospholipids (I) and (II) are not. Both the zinc-phthalocyanine complex and the phospholipids (I) and (II) are soluble in piperidine. All solvents are toxicologically harmless in the residual amounts of less than 1%, preferably less than 0.5%, present in the dry preparation.

When dimethyl sulfoxide or NMP is used, the zinc-phthalocyanine complex is dissolved in the minimum necessary amount of that solvent and the solution is combined with a second solution of the phospholipids that is miscible with the first solution of the zinc-phthalocyanine complex. In addition to the requirement of being miscible with the dimethyl sulfoxide solution, this second solvent is subject to the same toxicological requirements as regards the residual amounts present in the dry preparation. Such a suitable solvent in which the phospholipids (I) and (II) are completely soluble is, for example, tert-butanol.

The preparation of the dry preparation, preferably a lyophilisate, can be effected by modifying known methods, by first dissolving the introduced amount of the phospholipid, for example 1-hexadecanoyl-2-(9-cis-octadecenoyl)-3-sn-phosphatidyl choline, if required with gentle heating, in the amount of tert-butanol required for the dissolution process and combining that clear solution with a second solution comprising a defined amount of the zinc-phthalocyanine complex in an amount of dimethyl sulfoxide or NMP appropriate for the dissolution process. Alternatively, it is possible to dissolve the phospholipids (I) and (II) at approximately from 0° C. to room temperature, preferably at 0° C., and the zinc-phthalocyanine complex at from room temperature to approximately 40° C., preferably room temperature, in the minimum necessary amount of piperidine or in piperidine containing up to about 10%, preferably about 2 to 3%, water and to remove the solvent from that clear solution in order to produce the dry preparation. The clear solution in the said organic solvents can then be combined with the career liquid d) comprising water-soluble excipients, especially non-ionic additives such as lactose. The dry preparation can be prepared by removing the solvent mixture at low temperature below about 0° C. (lyophilisation) or at normal or elevated temperature (film formation). The solvent mixture used for the preparation of the dry preparation can also be dialysed for the purpose of purification and the dialysed aqueous solution, which contains no organic solvent, concentrated by ultrafiltration. The dry preparation is then prepared by removing water, preferably by lyophilisation. Measured amounts of the solution to be lyophilised can be introduced into suitable containers for a unit dose, such as ampoules, for example glass phials. The filled containers can then be frozen at about −40° to −50° C., especially at −45° C., and then lyophilised at a pressure of about 0.2–0.6 mbar by slowly heating to a final temperature of about 25°–35° C.

The solvent or solvent mixture comprising components a), b) and c) can be converted into a dry preparation also directly, without cooling, thermally in a larger vessel (film formation method). Freeze-drying from small vessels containing a unit dose is preferred, however, as this method avoids the operation of filling the dry preparation itself and therefore allows the accurate apportionment of unit doses from liquids.

Surprisingly, it has been possible using the said processes to prepare, reproducibly, dry preparations, especially lyophilisates, and liposome dispersions reconstitutable therefrom, that are stable and suitable for injection.

The present invention relates also to the use of the dry preparation obtainable in accordance with the said processes for the preparation of intravenously administrable liposome dispersions.

The present invention relates also to the use of the zinc-phthalocyanine complex and the phospholipid components of formula I and optionally of formula II for the preparation of dry preparations, especially lyophilisates, in accordance with the methods described hereinabove. The invention relates also to the use of the pharmaceutical compositions in a method for the therapeutic treatment of the human or animal body, especially in chemotherapy for the treatment of tumours. The liposome dispersion is administered parenterally, especially intravenously, and the carcinoma is irradiated with high-energy light, preferably with concentrated visible light (LASER).

The invention relates preferably to pharmaceutical compositions in the form of intravenously administrable liposome dispersions comprising a) the zinc-phthalocyanine complex, b) a synthetic, substantially pure phospholipid of formula I, wherein $R_1$ is n-dodecanoyl, n-tetradecanoyl, n-hexadecanoyl or n-octadecanoyl and $R_2$ is 9-cis-dodecenoyl, 9-cis-tetradecenoyl, 9-cis-hexadecenoyl, 9-cis-octadecenoyl or 9-cis-icosenoyl, $R_a$, $R_b$ and $R_c$ are methyl and n is two, optionally combined with a c) synthetic, substantially pure phospholipid of formula II, wherein $R_3$ and $R_4$ are identical and are 9-cis-dodecenoyl, 9-cis-tetradecenoyl, 9-cis-hexadecenoyl, 9-cis-octadecenoyl or 9-cis-icosenoyl, n is one and $Y^\oplus$ is the sodium ion, and d) a pharmaceutically acceptable carrier liquid and, optionally, water-soluble excipients suitable for intravenous dosage forms.

The invention relates preferably also to pharmaceutical compositions in the form of dry preparations comprising the said preferred components a), b), optionally combined with c), and d) water-soluble excipients suitable for intravenous dosage forms.

The invention relates especially to pharmaceutical compositions in the form of intravenously administrable liposome dispersions comprising a) the zinc-phthalocyanine complex, b) synthetic, substantially pure 1-n-hexadecanoyl-2-(9-cis-octadecenoyl)-3-sn-phosphatidyl choline (I), optionally combined with c) synthetic, substantially pure sodium 1,2-di(9-cis-octadecenoyl)-3-sn-phosphatidyl S-serine (II), and d) a pharmaceutically acceptable carrier liquid and, optionally, water-soluble excipients suitable for intravenous dosage forms.

The invention relates especially preferably to pharmaceutical compositions in the form of lyophilisates comprising a) the zinc-phthalocyanine complex, b) synthetic, substantially pure 1-n-hexadecanoyl-2-(9-cis-octadecenoyl)-3-sn-phosphatidyl choline (I), optionally combined with c) synthetic, substantially pure sodium 1,2-di(9-cis-octadecenoyl)-3-sn-phosphatidyl S-serine (II), and d) water-soluble excipients suitable for intravenous dosage forms.

The following Examples illustrate the invention.

EXAMPLE 1

1 mg of zinc-phthalocyanine, 70 mg of at least 95% pure 1-n-hexadecanoyl-2-(9-cis-octadecenoyl)-3-sn-phosphatidyl choline and 30 mg of at least 95% pure 1,2-di-(9-cis-octadecenoyl)-3-sn-phosphatidyl serine are dissolved in 2 ml of piperidine in a round-bottomed flask. The solution is sterile-filtered using an ACRODISC membrane filter ($2.2 \times 10^{-7}$ m) and the clear solution is introduced into phials.

After the solution has been frozen at $-40°$ C., the phials are dried in vacuo until a temperature of $25°$ C. has been reached and are sealed under an argon atmosphere.

Before use, 1.5 ml of sterile, calcium- and magnesium-free, phosphate-buffered (pH 7.2–7.4) sodium chloride solution (Dulbecco) are introduced into the above-mentioned dry preparation (lyophilisate) at room temperature using a sterile syringe and the phials are shaken for one minute on a standard laboratory shaker (Vortex, stage 7). The resulting liposome dispersion can be stored at $4°$ C. and is suitable for intravenous administration.

EXAMPLE 2

Depending upon the batch, from 0.1 to 1 mg of zinc-phthalocyanine and from 15 to 400 mg of a 7:3 mixture by weight of 95 to 100% pure 1-n-hexadecanoyl-2-(9-cis-octadecenoyl)-3-sn-phosphatidyl choline and 95 to 100% pure 1,2-di(9-cis-octadecenoyl)-3-sn-phosphatidyl serine are dissolved in 2 ml of piperidine in a round-bottomed flask. The solution is sterile-filtered using an ACRODISC membrane filter ($2.2 \times 10^{-7}$) and the clear solution is introduced into phials.

The phials are set in rotation at 150 rpm and the solvent is blown off in a stream of purified nitrogen filtered at 1 bar.

The phials are then evacuated in a vacuum of $6.0 \times 10^{-2}$ bar. The phials are sealed under an argon atmosphere. Before use, 1.5 ml of sterile, calcium- and magnesium-free, phosphate-buffered (pH 7.2–7.4) sodium chloride solution (Dulbecco) are added to the above-prepared film at room temperature using a syringe and the phials are shaken for 10 minutes on a standard laboratory shaker (stage 7). The resulting liposome dispersion can be stored at $4°$ C. and is suitable for intravenous administration.

EXAMPLE 3

In a manner analogous to Example 1, after being frozen the solutions mentioned in Example 2 are dried in vacuo and lyophilisates are prepared.

EXAMPLE 4

In a manner analogous to Examples 2 and 3 it is also possible to prepare solutions comprising from 5:5 to 9:1 mixtures by weight of 1-n-hexadecanoyl-2-(9-cis-octadecenoyl)-3-sn-phosphatidyl choline and 1,2-di(9-cis-octadecenoyl)-phosphatidyl serine.

EXAMPLE 5

125 ml of 95% pure 1-n-hexadecanoyl-2-(9-cis-octadecenoyl)-3-sn-phosphatidyl choline (Avanti, Polar Lipids) are dissolved in 0.5 ml of tert-butanol in a round-bottomed flask. 0.05 mg of zinc-phthalocyanine is dissolved separately in 0.5 ml of sterile dimethyl sulfoxide in a second round-bottomed flask.

The two solutions are combined and sterile-filtered through an ACRODISC membrane filter ($2.2 \times 10^{-7}$ m). After the introduction of the clear solution into a phial, it is frozen at $-80°$ C. The phials are dried in vacuo until a temperature of $25°$ C. has been reached and are sealed under an argon atmosphere.

The further process steps are carried out analogously to Example 1.

EXAMPLE 6

12.5 to 25 mg of 95% pure 1-n-hexadecanoyl-2-(9-cis-octadecenoyl)-3-sn-phosphatidyl choline (Avanti, Polar Lipids) are dissolved in 0.5 ml of tert-butanol in a round-bottomed flask. 0.05 mg of zinc-phthalocyanine is dissolved separately in 0.5 ml of sterile dimethyl sulfoxide in a second round-bottomed flask.

Analogously to Example 5 the two solutions are combined, sterile-filtered using an ACRODISC and introduced into phials. The phials are set in rotation at 150 rpm and the solvent is blown off in a stream of purified nitrogen filtered at 1 bar. The phials are then evacuated under a pure vacuum of $6.0 \times 10^{-2}$ bar. The phials are sealed under a protective argon atmosphere.

The further process steps are carried out analogously to Example 2.

EXAMPLE 7

0.5 mg of zinc-phthalocyanine and 250 mg of 95% pure 1-n-hexadecenoyl-2-(9-cis-octadecanoyl)-3-sn-phosphatidyl choline are dissolved in 1 ml of sterile piperidine in a round-bottomed flask. The solution is sterile-filtered using an ACRODISC membrane filter ($2.2 \times 10^{-7}$ m) and the clear solution is introduced into phials.

Analogously to Example 5 it is possible to produce a lyophilisate or, if desired, a film residue analogously to Example 6, which is then converted into an intravenously administrable liposome dispersion analogously to Example 1 or 2.

EXAMPLE 8

In a manner analogous to Example 7 it is possible to produce a lyophilisate or a film residue by dissolving 3 mg of zinc-phthalocyanine in 1 ml of sterile piperidine. From these dry preparations there is then produced an intravenously administrable liposome dispersion analogously to Example 1 or 2.

EXAMPLE 9

In a measuring flask at room temperature, depending upon the batch 200–400 mg of zinc-phthalocyanine are dissolved in 400 ml of piperidine puriss, and the solution is made up to 500 ml. In a second flask at room temperature, depending upon the batch 120–240 mg of a 7:3 mixture by weight of 95–100% pure 1-n-hexadecanoyl-2-(9-cis-octadecenoyl)-3-sn-phosphatidyl choline and 95–100% pure 1,2-di(9 -cis-octadecenoyl)-3-sn-phosphatidyl S-serine are dissolved in 6 ml of piperidine puriss., and 6–12 ml of the above zinc-phthalocyanine solution are added. The resulting solution is sterile-filtered using an ACRODISC membrane filter ($2.2 \times 10^{-7}$) and the clear solution is introduced into phials.

The further process steps are carried out analogously to Example 1.

EXAMPLE 10

In a measuring flask at room temperature, depending upon the batch 200–400 mg of zinc-phthalocyanine are dissolved in 400 ml of piperidine puriss, and the solution is made up to 500 ml. In a second flask, depending upon the batch 120–240 mg of a 7:3 mixture by weight of 95–100% pure 1-n-hexadecanoyl-2-(9-cis-octadecenoyl)-3-sn-phosphatidyl choline and 95–100% pure 1,2-di(9-cis-octadecenoyl)-3-sn-phosphatidyl S-serine are dissolved in 6 ml of a piperidine/water mixture 12–10%) at 0°–4° C. and at that temperature 6–12 ml of the above zinc-phthalocyanine solution are added dropwise thereto. The resulting solution is sterile-filtered using an ACRODISC membrane filter ($2.2 \times 10^{-7}$) and the clear solution is introduced into phials.

The further process steps are carried out analogously to Example 2.

EXAMPLE 11

After sterile-filtration, a solution of zinc-phthalocyanine and lipid mixture prepared according to Example 9 or Example 10 is not introduced into phials but is lyophilised in a batch process. Aliquot amounts of the resulting lyophilisate are converted into a liposome dispersion analogously to Example 1.

EXAMPLE 12

100 mg of zinc-phthalocyanine, 7000 mg of 95% pure 1-n-hexadecanoyl-2-(9-cis-octadecanoyl)-3-sn-phosphatidyl choline (POPC) and 3000 mg of 95% pure sodium 1,2-di(9-cis-octadecanoyl)-3-sn-phosphatidyl S-serine (OOPS) are dissolved in 205 ml of freshly distilled piperidine in a round-bottomed flask.

To that solution there are added, with stirring, 2000 ml of 9.75% W/V aqueous lactose solution. After the pH value has been adjusted to 7.0 by the addition of dilute HCl, the resulting dispersion is concentrated to a concentration of 0.5 mg of zinc-phthalocyanine/ml and dialysed against 2000 ml of 9.75% lactose using a Millipore Minitan® tangential dialysis apparatus.

The resulting lactose-containing dispersion is then sterile-filtered using an ACRODISC membrane filter ($2.2 \times 10^{-7}$) and introduced into phials (2 ml per phial containing 1 mg of zinc-phthalocyanine). After the dispersion has been frozen at −40° C., the phials are dried in vacuo until a temperature of 25° C. has been reached and are sealed under an argon atmosphere.

The resulting dry preparations can be stored at 4° C. for several years.

Before administration, 2.0 ml of water are injected using a sterile syringe into a dry preparation (lyophilisate) in a phial at room temperature. After a maximum dissolution time of one minute there is formed a liposome dispersion suitable for intravenous administration.

EXAMPLE 13

In a manner analogous to Example 12, it is possible to carry out the process with 10 000 mg of POPC.

EXAMPLE 14

In a manner analogous to Example 13, it is possible to carry out the process with 300 mg of POPC or 210 mg of POPC and 90 mg of OOPS.

EXAMPLE 15

In a flask, 35 g of POPC and 15 g of OOPS are dissolved in 500 ml of tertiary butanol, with stirring, at 40° C. In a further flask, 0.5 g of zinc-phthalocyanine is dissolved in 125 ml of NMP (ultrasonic bath).

The two solutions are mixed together, the dye solution being poured into the tertiary butanol solution. The mixture is heated to 40° C. in order to obtain a clear solution. Using a dynamic mixer, that solution is mixed with 10 liters of lactose medium that has been cooled to 4° C. and that contains per liter 94.9 g of lactose for injection and 24 g of sodium chloride.

The organic phase is pumped at a rate of 107 ml/min and the lactose solution at a rate of 1714 ml/min into the dynamic mixer, which is operated at a pressure of 3 bar.

The resulting blue, slightly opalescent dispersion (10625 ml) is concentrated to 1 liter and then dialysed against 10 liters of lactose medium using a Millipore tangential dialysis apparatus.

The further procedure is described in Example 12.

EXAMPLE 16

In a manner analogous to Example 15, 3.5 g of POPC and 1.5 g of OOPS are dissolved in 100 ml of tert-butanol and mixed with 25 ml of NMP and 100 mg of zinc-phthalocyanine. The organic phase is then mixed with 2 liters of lactose medium (25 g of lactose and 0.064 g of NaCl per liter). The dialysis medium has the same composition.

EXAMPLE 17

In a manner analogous to Example 16, the organic phase is mixed with 2 liters of lactose medium containing 50 g of lactose and 0.127 g of NaCl per liter.

EXAMPLE 18

In a manner analogous to Example 15, 10.5 g of POPC and 4.5 g of OOPS are dissolved in 200 ml of tert-butanol and mixed with 50 ml of NMP containing 200 mg of zinc-phthalocyanine. The organic phase is mixed with 4 liters of lactose medium containing 37.5 g of lactose and 0.095 g of NaCl per liter. The dialysis medium has the same composition.

EXAMPLE 19

In a manner analogous to Example 18, the organic phase is mixed with 4 liters of lactose solution containing 75 g of lactose and 0.1905 g of NaCl per liter. The dialysis medium has the same composition.

EXAMPLE 20

In a manner analogous to Example 15, 3.5 g of POPC and 1.5 g of OOPS are dissolved in 200 ml of tert-butanol and mixed with 50 ml of NMP containing 200 mg of zinc-phthalocyanine. The organic phase is mixed with 4 liters of lactose medium containing 25 g of lactose and 0.064 g of NaCl per liter. The dialysis medium has the same composition.

EXAMPLE 21

In a flask, 40 g of POPC and 10 g of OOPS are dissolved in 500 ml of tertiary butanol, with stirring, at 50° C. In a further flask, 0.5 g of zinc-phthalocyanine is dissolved in 125 ml of NMP (ultrasonic bath).

The two solutions are mixed together, the dye solution being poured into the tertiary butanol solution. The mixture is heated to 50° C. in order to obtain a clear solution. Using a dynamic mixer, that solution is mixed with 10 liters of lactose medium that has been cooled to 4° C. and that contains per liter 94.6 g of lactose for injection and 27 g of sodium chloride.

The organic phase is pumped at a rate of 107 ml/min and the lactose solution at a rate of 1714 ml/min into the dynamic mixer, which is operated at a pressure of 3 bar.

The resulting blue, slightly opalescent dispersion (10625 ml) is concentrated to 1 liter and then dialysed against 10 liters of lactose medium using a Millipore tangential dialysis apparatus.

The further procedure is described in Example 12.

EXAMPLE 22

In a flask, 45 g of POPC and 5 g of OOPS are dissolved in 500 ml of tertiary butanol, with stirring, at 50° C. In a further flask, 0.5 g of zinc-phthalocyanine is dissolved in 125 ml of NMP (ultrasonic bath).

The two solutions are mixed together, the dye solution being poured into the tertiary butanol solution. The mixture is heated to 50° C. in order to obtain a clear solution. Using a dynamic mixer, that solution is mixed with 10 liters of lactose medium that has been cooled to 4° C. and that contains per liter 94.6 g of lactose for injection and 27 g of sodium chloride.

The organic phase is pumped at a rate of 107 ml/min and the lactose solution at a rate of 1714 ml/min into the dynamic mixer, which is operated at a pressure of 3 bar.

The resulting blue, slightly opalescent dispersion (10625 ml) is concentrated to 1 liter and then dialysed against 10 liters of lactose medium using a Millipore tangential dialysis apparatus.

The further procedure is described in Example 12.

What is claimed is:

1. A method of treating tumors which respond to photodynamic chemotherapy consisting essentially of administering an amount effective to therapeutically treat a tumor of a pharmaceutical liposome composition to an animal in need thereof, said composition comprising:

a) the zinc-phthalocyanine complex in an amount of 0.1 to 5% by weight based on the total amount of the phospholipid (b) dissolved in N-methyl-2-pyrrolidone;

b) at least one synthetic, substantially pure phospholipid dissolved in tert-butanol, said phospholipid selected from the group consisting of
      i) a phospholipid of formula I

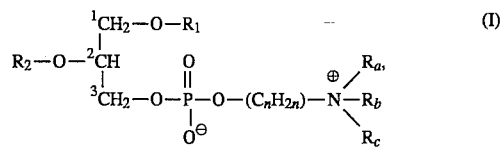

wherein $R_1$ is $C_{10}$–$C_{20}$ alkanoyl having an even number of carbon atoms, $R_2$ is $C_{10}$–$C_{20}$ alkenoyl having an even number of carbon atoms, $R_a$, $R_b$ and $R_c$ are hydrogen or $C_1$–$C_4$ alkyl and n is an integer from two to four, and
      ii) a phospholipid of formula II

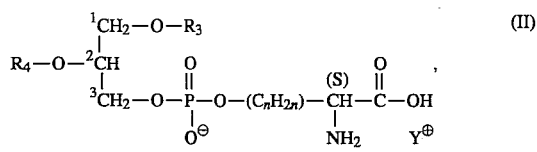

wherein $R_3$ and $R_4$ are each independently of the other $C_{10}$–$C_2$ alkenoyl having an even number of carbon atoms, n is an integer from one to three and $Y^\oplus$ is the cation of a pharmaceutically acceptable base; and c) a pharmaceutically acceptable carrier liquid.

2. The method of claim 1, wherein the pharmaceutical composition further comprises at least one water-soluble excipient suitable for a parenteral dosage form.

* * * * *